United States Patent
Gazelakis et al.

(10) Patent No.: US 11,660,168 B2
(45) Date of Patent: May 30, 2023

(54) DENTAL IMPLANT

(71) Applicant: THE UNIVERSITY OF MELBOURNE, Melbourne (AU)

(72) Inventors: Efthimios Gazelakis, Melbourne (AU); Joseph Palamara, Melbourne (AU); Roy Judge, Melbourne (AU)

(73) Assignee: The University of Melbourne, Melbourne (AU)

( * ) Notice: Subject to any disclaimer, the term of this patent is extended or adjusted under 35 U.S.C. 154(b) by 0 days.

(21) Appl. No.: 15/572,442

(22) PCT Filed: May 6, 2016

(86) PCT No.: PCT/AU2016/050339
§ 371 (c)(1),
(2) Date: Nov. 7, 2017

(87) PCT Pub. No.: WO2016/176744
PCT Pub. Date: Nov. 10, 2016

(65) Prior Publication Data
US 2018/0140389 A1    May 24, 2018

(30) Foreign Application Priority Data

May 7, 2015   (AU) ................................ 2015901651
Mar. 10, 2016 (AU) ................................ 2016900901

(51) Int. Cl.
*A61C 8/00* (2006.01)
*A61F 2/28* (2006.01)
(Continued)

(52) U.S. Cl.
CPC ...... *A61C 8/0009* (2013.01); *A61B 17/06166* (2013.01); *A61C 8/001* (2013.01);
(Continued)

(58) Field of Classification Search
CPC ..... A61C 8/0009; A61C 8/001; A61C 8/0022; A61C 2008/0046; A61C 8/0066;
(Continued)

(56) References Cited

U.S. PATENT DOCUMENTS 3,797,113 A * 3/1974 Brainin .................. A61C 8/005
                                                    433/173
3,849,887 A * 11/1974 Brainin ................ A61C 8/0012
                                                    433/173
(Continued)

FOREIGN PATENT DOCUMENTS

CN    1750797 A *  3/2006  .......... A61C 8/0048
EP    0361526 A2   4/1990
(Continued)

OTHER PUBLICATIONS

Young-Ku Heo, CN 1750797 A, Screw-retaining And Implant Abutment Retaining The Mending Method Of Repairing Method And A Screw-cement Cementing Agent (Year: 2006).*

*Primary Examiner* — Ralph A Lewis
*Assistant Examiner* — Mirayda A Aponte
(74) *Attorney, Agent, or Firm* — Workman Nydegger

(57) ABSTRACT

A dental implant adapted for implanting within a jaw bone, the implant comprising a horizontally-oriented body having a length extending in the mesial-distal direction of the jaw bone, the body having a threaded cavity dimensioned for receiving a prosthetic abutment, and wherein the cavity comprises an opening that is located wholly within a bucco-lingual width of the body.

25 Claims, 14 Drawing Sheets

(51) Int. Cl.
*A61B 17/06* (2006.01)
*A61F 2/30* (2006.01)

(52) U.S. Cl.
CPC .......... *A61C 8/0018* (2013.01); *A61C 8/0022* (2013.01); *A61C 8/0066* (2013.01); *A61C 8/0068* (2013.01); *A61C 8/0071* (2013.01); *A61C 8/0075* (2013.01); *A61C 8/0078* (2013.01); *A61F 2/2803* (2013.01); *A61C 2008/0046* (2013.01); *A61F 2002/30116* (2013.01); *A61F 2002/30261* (2013.01); *A61F 2002/30405* (2013.01); *A61F 2002/30807* (2013.01); *A61F 2002/30828* (2013.01); *A61F 2002/30891* (2013.01); *A61F 2310/00023* (2013.01)

(58) Field of Classification Search
CPC ... A61C 8/0068; A61C 8/0071; A61C 8/0018; A61C 8/0075; A61C 8/0078; A61C 8/0031; A61C 8/00; A61C 8/0037; A61B 17/06166; A61F 2/2803; A61F 2002/30116; A61F 2002/30261; A61F 2002/30405; A61F 2002/30807; A61F 2002/30828; A61F 2002/30891; A61F 2310/00023
USPC .............................. 433/172–174, 176, 201.1
See application file for complete search history.

(56) References Cited

U.S. PATENT DOCUMENTS

| | | | | |
|---|---|---|---|---|
| 3,849,888 A | * | 11/1974 | Linkow | A61C 8/0075 433/176 |
| 4,187,609 A | * | 2/1980 | Edelman | A61C 8/001 433/176 |
| 4,447,209 A | * | 5/1984 | Sutter | A61C 8/00 433/173 |
| 4,964,801 A | * | 10/1990 | Kawahara | A61C 8/001 433/173 |
| 5,102,336 A | * | 4/1992 | Linkow | A61C 8/0019 433/176 |
| 2004/0033469 A1 | * | 2/2004 | Blacklock | A61C 8/0022 433/173 |
| 2004/0258732 A1 | * | 12/2004 | Shikinami | A61L 27/446 424/426 |
| 2005/0042288 A1 | * | 2/2005 | Koblish | A61B 17/866 424/466 |
| 2005/0159754 A1 | * | 7/2005 | Odrich | A61B 17/666 606/86 R |
| 2007/0059666 A1 | * | 3/2007 | Zickman | A61C 8/0066 433/173 |
| 2007/0148622 A1 | * | 6/2007 | Gogarnoiu | A61C 3/03 433/173 |
| 2008/0039837 A1 | * | 2/2008 | Gambale | A61C 8/0074 606/60 |
| 2010/0285427 A1 | * | 11/2010 | Hung | A61C 8/0089 433/174 |
| 2011/0008754 A1 | * | 1/2011 | Bassett | A61C 8/0012 433/175 |
| 2011/0287381 A1 | * | 11/2011 | Sanders | A61C 1/084 433/75 |
| 2012/0115105 A1 | * | 5/2012 | Schneider | A61C 8/0077 433/173 |
| 2013/0288200 A1 | * | 10/2013 | Battula | A61C 8/0006 433/173 |
| 2013/0309632 A1 | * | 11/2013 | Sanders | A61C 8/0022 433/174 |
| 2016/0045290 A1 | * | 2/2016 | Poovey | A61C 8/0018 433/174 |
| 2016/0235503 A1 | * | 8/2016 | Haydar | A61C 8/0037 |
| 2018/0177573 A1 | * | 6/2018 | Denton | A61C 8/0069 |
| 2018/0344434 A1 | * | 12/2018 | Poovey | A61C 8/0001 |

FOREIGN PATENT DOCUMENTS

| | | | | |
|---|---|---|---|---|
| WO | WO1997043978 A1 | 11/1997 | | |
| WO | WO2004064664 A1 | 8/2004 | | |
| WO | WO2004082504 A2 | 9/2004 | | |
| WO | WO-2011069978 A1 | * | 6/2011 | .......... A61C 8/0019 |
| WO | WO2011069978 A1 | 6/2011 | | |

* cited by examiner

DENTAL IMPLANT

FIELD OF THE INVENTION

The invention relates to a dental implant and in particular to a dental implant for use in restoration of the resorbed posterior alveolar ridge.

BACKGROUND OF THE INVENTION

Implants are commonly used to replace teeth that have been extracted from a patient. Typically teeth that have been extracted from the rear of the lower jawbone, the posterior alveolar ridge, have been replaced with conventional vertically oriented implants. The conventional implants are suited to patients in the early stages of osseous healing and provide a viable prosthodontic option. Threaded implants are popular since they appear to replicate the lost cylindrical root structure of the extracted tooth.

Vertically orientated implants require a minimum height of bone into which the implant can be secured. Where the bone height is insufficient, short cylindrical implants can be used. However, short cylindrical implants are less able to withstand the loads applied to the implant in the long term and are subject to a higher rate of failure compared to longer implants.

A further problem arises when a patient requires an implant in the posterior alveolar ridge many years or decades after the original tooth has been extracted. In that time the alveolar ridge will have been at least partially, sometimes substantially resorbed, resulting in the jaw bone having significantly reduced height and width to accommodate even short cylindrical implants as described above. The mesial-distal length of the ridge is in essence however, naturally maintained.

A further consideration when placing a dental implant is the location of the central nerve of the lower jaw, which if traumatised upon implant surgery, could result in permanent numbness, altered sensation and facial dribbling of saliva. This becomes particularly important when the posterior alveolar ridge has been heavily resorbed with insufficient bone structure provided for an implant without complex grafting procedures.

Other problems associated with placing implants in the posterior alveolar ridge after a length of time is the super-eruption of more distal opposing teeth, complex grafting procedures to augment the ridge, and the use of short cylindrical implants which as noted above have a higher failure rate than longer implants.

If short cylindrical implants are chosen, clinical experience has indicated that the minimum diameter in short cylindrical implants (<7 mm) is ideally 5 mm. One problem facing the clinician is that the "pointy" alveolar ridge in these cases means that although the mesial-distal preparation of the 5 mm radius is accommodated for, the buccolingual dimension necessitates a loss of vertical crestal height in the rim of the preparation. This means either a deeper placement or an attempt to cover exposed protruding threads. Since a deeper preparation is not possible in these circumstances, the latter approach is needed, with all its associated complexities.

The present invention seeks to at least in part alleviate the problems identified above associated with conventional implants, particularly in the posterior alveolar ridge.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention is based on the observation that even in a heavily resorbed posterior alveolar ridge the mesial-distal length of the bone is preserved. This observation has led to the creation of a horizontally oriented dental implant.

According to one aspect of the present invention, there is provided a dental implant adapted for implanting within a jaw bone, the implant comprising a horizontally-oriented body having a length extending in the mesial-distal direction of the jaw bone, the body having a threaded cavity dimensioned for receiving a prosthetic abutment, and wherein the cavity comprises an opening that is located wholly within a buccolingual width of the body.

Preferably, the body is configured to substantially reside within an imaginary boundary of a generally rectangular prism shape.

Preferably, the body is a rectangular prism having a minimum buccolingual width of 4 mm, an apical-occlusal height of 5.25 mm, and a minimum mesial-distal length of 6 mm.

Preferably, the body has substantially the same buccolingual width along its mesial-distal length.

Preferably, the body has two end faces, two side faces, and a base, that form external wall surfaces of the body.

Preferably, one or more external wall surfaces of the body are provided with a plurality of surface geometry for enhancing the surface area of the body. Preferably, the plurality of surface geometry includes any one or more of the following non-limiting examples: grooved, ridged, gouged, wavy or cratered.

Preferably, the surface of the body comprises a plurality of grooves aligned with the horizontal axis of the body. Preferably, the plurality of grooves are provided on the two end faces and the two side faces. Preferably, the plurality of grooves are provided on the base of the body. Preferably, the shape of the grooves includes any one or more of the following non-limiting examples: v-shaped, rounded, circular, semi-circular, triangular, trapezoidal, or irregular in shape. Preferably, the grooves are of equal width. Preferably, the grooves are smaller in width in a crestal portion of the body.

Preferably, the base of the body is provided with rounded corners at the junction with the respective side and end faces. Alternatively, the base of the body is flat and with straight side walls.

Preferably, the body is formed with curved ends. Alternatively, the body is formed with straight ends.

Preferably, the body is substantially trapezoidal in shape with a wider crestal portion and a smaller apical portion.

Preferably, the body is formed of titanium.

Preferably, the threaded cavity has a lower end and an upper end, wherein a cylindrical internal thread is provided at the lower end of the cavity and a truncated conical portion is provided at the upper end of the cavity.

Preferably, one or more surface recesses are provided in the upper surface of the dental implant for receiving anti-rotational projections, and the surface recesses are confluent with the cavity.

According to another aspect of the present invention, there is provided a dental implant system for implanting within a jaw bone, the system comprising a dental implant comprising a horizontally-oriented body having a length extending in the mesial-distal direction of the jaw bone, the body having one or more threaded cavity, wherein the cavity comprises an opening that is located wholly within a buccolingual width of the body; at least one prosthetic abutment comprising an external tapered connection and an internal recess, the at least one prosthetic abutment is dimensioned and adapted to be received by the cavity by way of interference fit; and an abutment fastener for securing the abutment to the body, wherein the fastener is received within the internal recess of the abutment and secured to the threaded cavity.

Preferably, the prosthetic abutment is provided on its outer surface with a pair of opposed projections. Preferably, the shape of the projections includes any one or more of the following non-limiting examples: triangular or semi-circular prisms.

Preferably, the body further comprises at least one surface recess having dimensions corresponding to the anti-rotational projections, such that, in use, the prosthetic abutment is received in the truncated conical recess and secured in place such that the opposed projections align with and engage the corresponding surface recesses.

According to another aspect of the present invention, there is provided a prosthetic abutment for use with a dental implant, the prosthetic abutment including a tapered wall, and adapted to receive an abutment fastener centrally within the prosthetic abutment, such that in use the prosthetic abutment can be secured to the dental implant.

Preferably, the prosthetic abutment is provided on its outer surface with one or more projections. Preferably, the projections are triangular or semi-circular prisms. Preferably, the projections are a pair of opposed projections. Preferably, the one or more projections are configured to engage corresponding surface recesses on a dental implant.

Preferably, the prosthetic abutment is adapted for use with any one of the above described dental implant.

According to another aspect of the present invention, there is provided a method for restoring a resorbed posterior alveolar ridge of a jaw bone using a dental implant system, the method comprising the steps of: providing a dental implant comprising a horizontally-oriented body having a length extending in the mesial-distal direction of the jaw bone, the body having a threaded cavity, wherein the cavity comprises an opening that is located wholly within a buccolingual width of the body; and providing a prosthetic abutment having an internal recess to the dental implant by way of securing an abutment fastener through the internal recess of the prosthetic abutment to the threaded cavity of the body.

Preferably, the above method further comprises the steps of: creating an implant site at the resorbed posterior alveolar ridge of a jaw bone; seating the dental implant at the implant site; filling the implant site with bone tissue materials harvested during the excavation of the implant site; and closing the implant site.

Also described herein is a method of implanting a dental implant into a jaw bone, the method comprising: making one or more incisions in the alveolar mucosa to produce an implant site generally conforming to the dental implant; harvesting bone tissue debris and the osteotomy block; implanting the dental implant in the implant site; filling the implant site using the harvested mucoperiosteum; and closing the implant site by suturing the alveolar mucosa.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

The invention will now be described, by way of example only, with reference to the accompanying drawings, in which.

DETAILED DESCRIPTION OF THE EMBODIMENTS

The applicant has identified that dental clinicians are faced with the problem of placing implants in the posterior alveolus decades after the teeth were extracted, and that it is desirable for there to be provided a dental implant for use in the restoration of the resorbed posterior alveolar ridge.

Figure 1A:
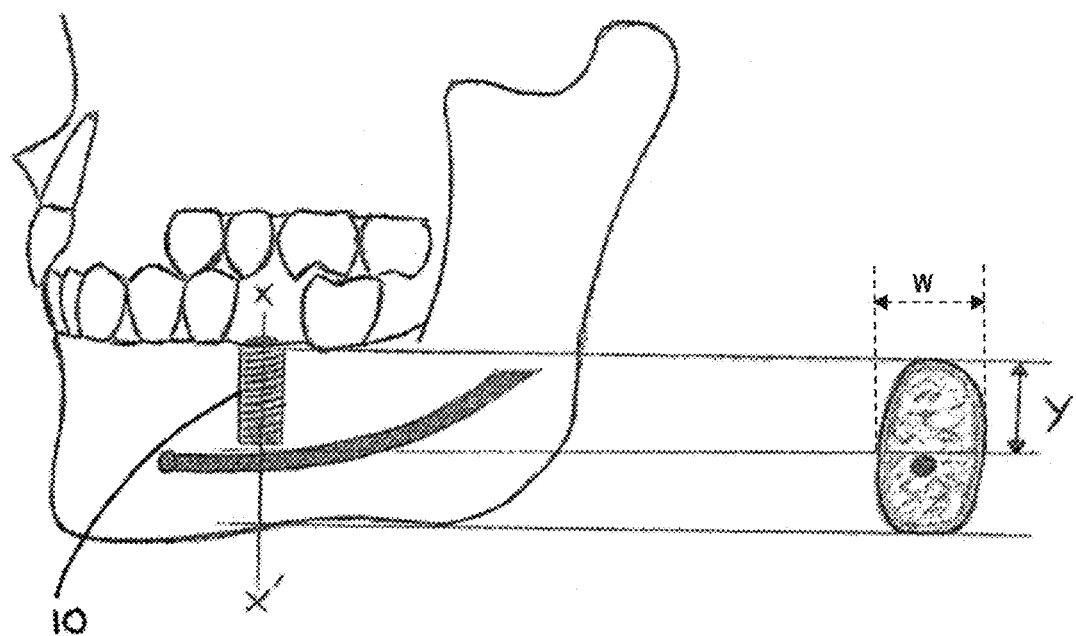
FIG. 1A illustrates the side view of the posterior alveolar ridge shortly after a tooth extraction.

FIG. 1A illustrates the typical shape of the posterior alveolar ridge shortly after a tooth extraction. The ridge is in the early stages of osseous healing and essentially retains its original bone shape. The inferior alveolar nerve is shown within the bone. Any trauma to the nerve during implant surgery can cause permanent numbness, altered sensation, and facial dribbling of saliva. It is therefore essential that the nerve is not impacted upon.

The vertical cross section of the bone is also shown in FIGS. 1A and 1t will be noted that it is generally symmetrical in shape with the alveolar nerve in the lower half.

Figure 1B:
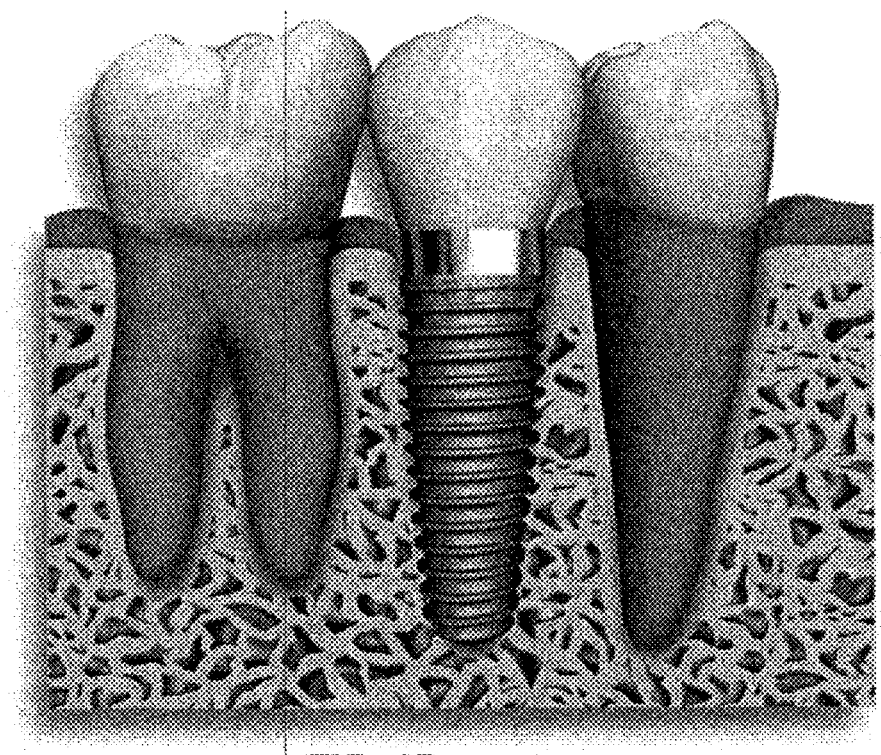
FIG. 1B depicts a number of conventional cylindrical dental implants.

When the alveolar ridge is shaped as shown in FIG. 1A, it is possible to employ a conventional cylindrical vertically oriented implant 10 and secured to the jaw bone as shown in FIG. 1B. There is typically sufficient buccolingual width W and corresponding apical-occlusal height Y to support a long implant without impacting the alveolar nerve.

Figure 2A:
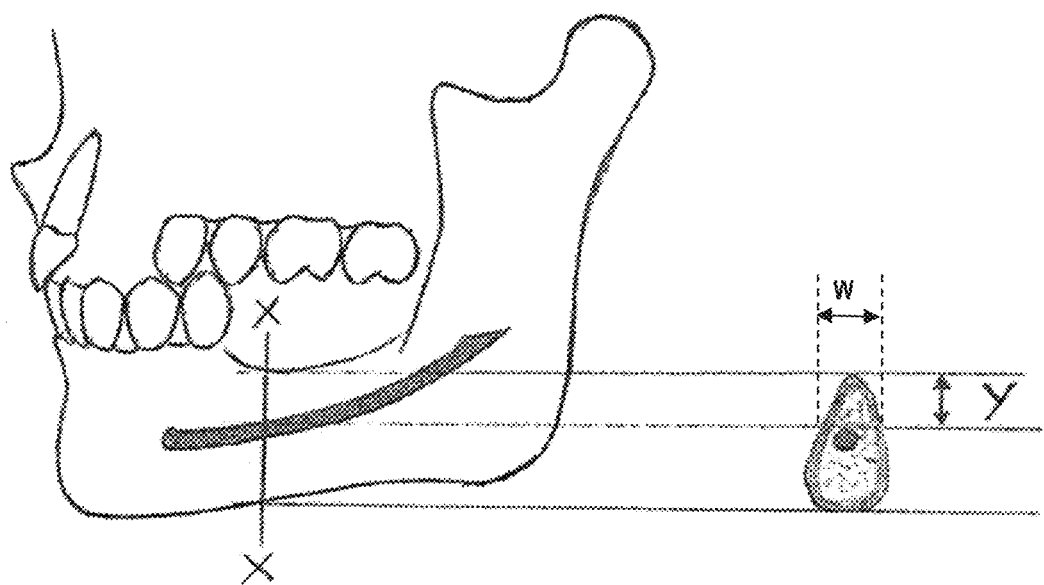
FIG. 2A illustrates the side view of a resorbed posterior alveolar ridge.
Figure 2B:
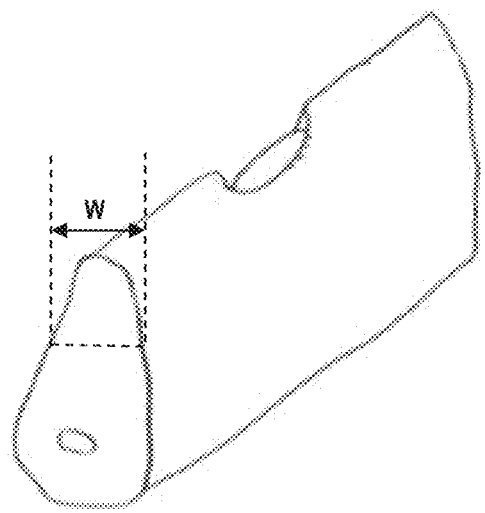
FIG. 2B is a schematic perspective drawing of a resorbed posterior alveolar ridge having a reduced buccolingual width for supporting conventional cylindrical dental implants.

FIGS. 2A and 2B illustrate a typical shape of the posterior alveolar ridge many years after a tooth extraction. It can be readily observed that the buccolingual width W and corresponding apical-occlusal height Y between the surface of the ridge and the nerve is significantly reduced compared to FIG. 1A. Resorption of the ridge also leads to the upper part of the ridge becoming more "pointy" as the bone narrows. The volume of bone that is available to support an implant without impinging on the nerve is therefore greatly reduced. As mentioned above, the use of a short cylindrical implant in the resorbed posterior alveolar ridge is restricted in both the height and width dimensions and is typically prone to a high failure rate.

FIGS. 1A and 2A show that the mesial-distal length of the ridge is not affected by resorption of the bone. The present invention therefore takes advantage of the length of bone remaining after resorption.

Figure 3:
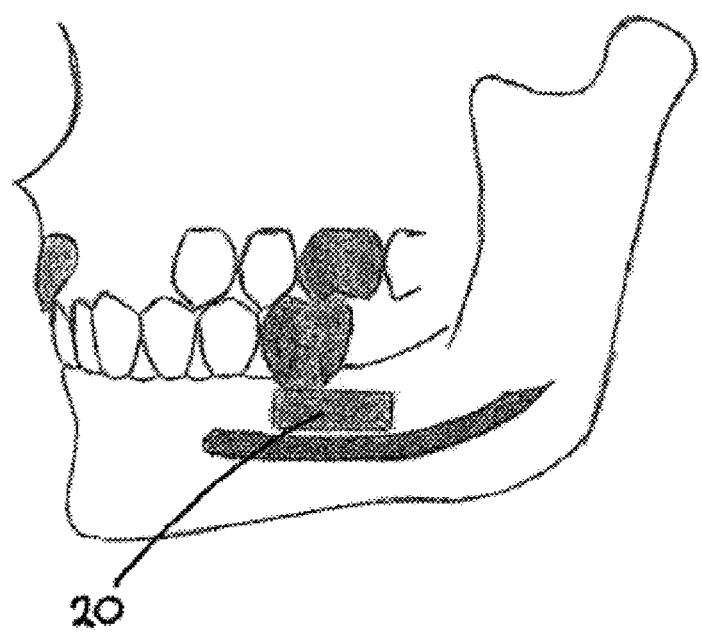
FIG. 3 illustrates the side view of the posterior alveolar ridge with an implant body in the form of a rectangular prism according to an embodiment of the invention.
Figure 4:
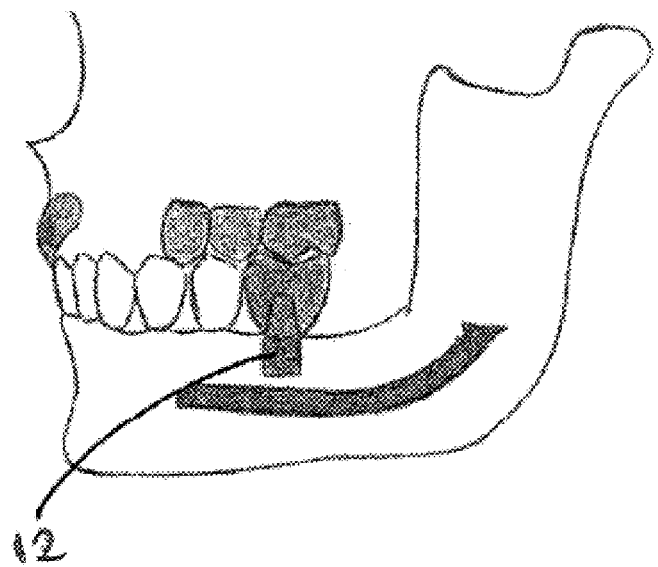
FIG. 4 illustrates the side view of the posterior alveolar ridge with a conventional short cylindrical implant.

A dental implant 20 of a preferred embodiment of the invention is illustrated in FIG. 3 while a conventional short cylindrical implant 12 is shown in FIG. 4. The dental implant 20 has a horizontally-oriented body, in the form of a rectangular prism or block, having a length that is extended substantially in the direction of the mesial-distal length of the jaw bone. Advantageously, this configuration provides a stable support structure for receiving prosthetic abutments (such as a prosthetic false tooth or a healing abutment) and provides a greater surface area available for osseointegration when compared to a conventional short cylindrical implant.

The greater surface area of the implant 20, when compared to a conventional short cylindrical implant, can be illustrated by the following example. For a horizontally oriented body of width W, depth D and length L, the total surface area is $2DW+2LD+LW$ (omitting the crestal portion). A vertically oriented perfect cylinder, of radius R, and depth D, has a surface area of $D2\pi R+\pi R^2$ (omitting the crestal portion). Assuming the length of the horizontally oriented body equals the depth of the cylinder, both being 10 mm, the width and depth of the body are 4 mm and 6 mm respectively, and the radius of the cylinder is 2 mm, (omitting the crestal portion of the cylinder and the body), the total surface area of the cylinder is 138.16 mm$^2$ as opposed to 208 mm$^2$ for the body.

More specifically, the implant 20 having a horizontally-oriented body allows for a structure that minimalises the optimal buccolingual width W and the apical-occlusal height Y required for the implant 20 to readily fit into the resorbed posterior alveolar ridge, while providing a surface area that is substantially equivalent to a conventional (long) cylindrical implant and a much greater surface area than a short cylindrical implant. Furthermore, an implant 20 with the synergistic combination of a higher surface area and a horizontal orientation in the mesial-distal direction allows the volume of any remaining resorbed posterior alveolar ridge to be efficiently utilised with the additional advantage of providing a greater surface area for bone cell osseointegration. Additionally, the wider-body and horizontally-oriented configuration of the implant 20 allows lateral forces to be distributed over a greater area of the implant 20 in use, resulting in a greater distributed load, which is especially important for the application of dental implants in a resorbed alveolar ridge with narrowed bones where the bone structure has a reduced ability to withstand lateral forces. Experiments as discussed later in the section have shown that an implant 20 and abutment system embodying the present invention is able to withstand a force in excess of 2,000 N, which far exceeds the physiological loads that can be generated in an oral environment.

The applicant notes that osseointegration is a process that occurs on a molecular level, in which an interface is formed directly between an implant and bone tissues without an interposed soft issue layer. This osseointegration process is dependent on the surface properties of the implant on a nanometre scale rather than an overall shape of the implant.

The dental implant 20 embodiments of the invention are shown in greater detail with reference to FIGS. 5A to 5F of the drawings. In one embodiment, the dental implant 20 comprises a body in the form of a rectangular prism having a length L in extending in the direction of the mesial-distal length, a width W across the buccolingual width, and an apical-occlusal height Y. It is to be appreciated that the implant 20 may have a buccolingual width W of at least 4 mm, an apical-occlusal height Y of at least 5.25 mm, and a mesial-distal length L of at least 6 mm. It is also preferable that the mesial-distal length L of the implant does not exceed 18 mm.

With reference to FIGS. 5A-5C and 11A-11C, the implant 20 has a rounded base 22a and curved end walls 24a, 26a. Side walls 28, 30 are flat and perpendicular to upper surface 32. The rounded base 22a has a semi-circular contour in the mesial-distal direction and rounded corners joining the side walls 28, 30 and end walls 24a, 26a in the buccolingual direction. In this configuration, the base 22a and/or corners of the implant 20 between the end walls 24a, 26a and the side walls 28, 30 are rounded to avoid sharp-angled edges (which produce highly concentrated point-stress distributions). The rounded corners serve the purpose of minimising concentration of stress forces at the corners of the implant 20 so that the implant could withstand greater loading forces. In other configurations, as illustrated in FIGS. 6A-6C and 9A-9C, the implant 20 has a substantially flat base 22b and substantially straight end walls 24b, 26b. The implant 20 may also have substantially the same buccolingual width W at each end. In certain configurations, the implant 20 could also have a generally trapezoidal cross-section along its buccolingual width W and/or mesial-distal length L, such that the implant 20 has a wider crestal portion and a smaller apical portion. It will be appreciated that the implant 20 may vary in its precise shape while still residing within an imaginary boundary of a generally rectangular prism shape.

In some configurations, the side walls 28, 30 of the implant 20 curves along the mesial-distal length L of the jaw bone such that the implant 20 substantially matches the curvature of the posterior alveolar ridge. In this sense, the degree of curvature of the implant 20 length L could be customised to better match a patient's morphology.

The implant 20 may be provided with grooves 33 for increasing the total surface area available for osseointegration between the implant 20 and the alveolar ridge. The grooves may be located on any surfaces 22a, 22b, 24a, 24b, 26a, 26b, 28, 30 of the implant 20. In certain embodiments, with reference to FIGS. 5A-5C, the surfaces of side and end walls 24a, 26a, 28, 30 are provided with a plurality of horizontally aligned grooves 33. In some embodiments, with reference to FIG. 7A-7C, the base 22 of the implant may also be provided with grooves. The grooves 33 may be generally V-shaped but grooves of other shapes may also be employed. Non-limiting examples of grooves 33 shapes include: generally rounded, circular, semi-circular, triangular, trapezoidal, or irregular in shape. The grooves 33 may be symmetrically or asymmetrically arranged and either horizontally or vertically oriented. In some instances, with reference to FIGS. 6A-6C and 9A-9C, the grooves 33 can be located partially along the side and end walls 24b, 26b, 28, 30, and preferably arranged towards the centre along the apical-occlusal height Y of the walls. In other instances, the grooves 33 are located on the upper and lower portions of the side and end walls 24b, 26b, 28, 30. The spacing and dimensions of the grooves 33 may also be varied. The number of grooves provided can also vary. It is to be appreciated that the preferable depth of the groove is 0.5 mm.

In other configurations, the external surfaces of the implant 20 may be provided with a surface geometry that is ridged, gouged, wavy or cratered for creating a surface roughness to improve the surface area available for osseointegration. It is to be appreciated that a standardised arithmetic deviation from a mean plane of approximately 1 micrometer is the preferred degree of surface roughness. This goes towards achieving the desired osseointegration during induced osteoblastic function.

Figure 5A:
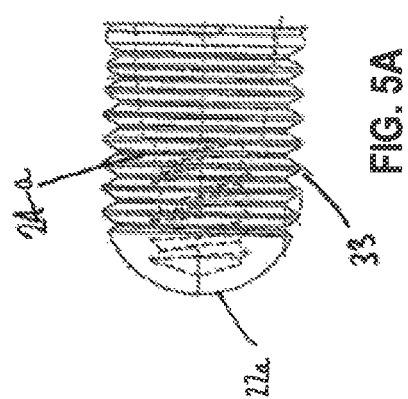
FIGS. 5A to 5C illustrate diagrammatic front, plan and side views of dental implants according to preferred embodiments of the invention.
Figure 5B:
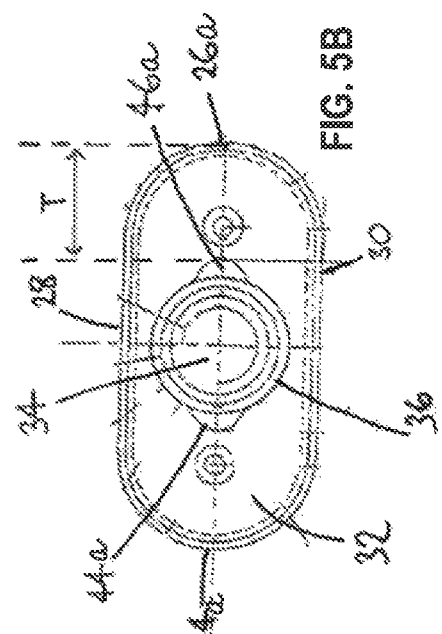
Figure 5C:
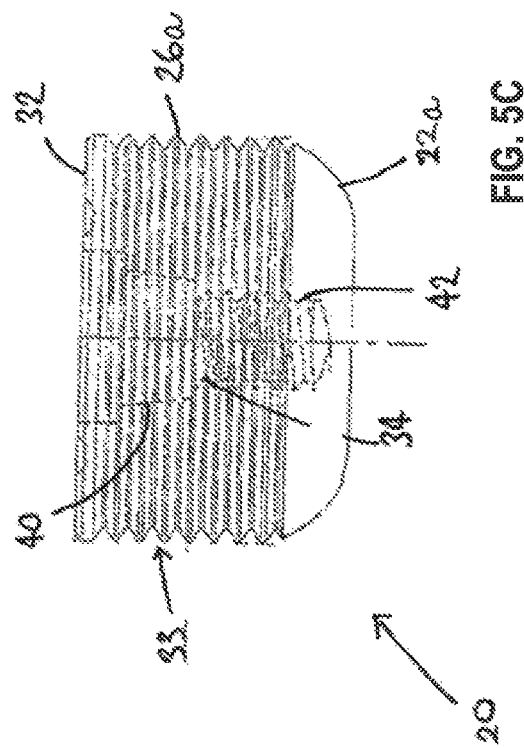
Figure 6A:
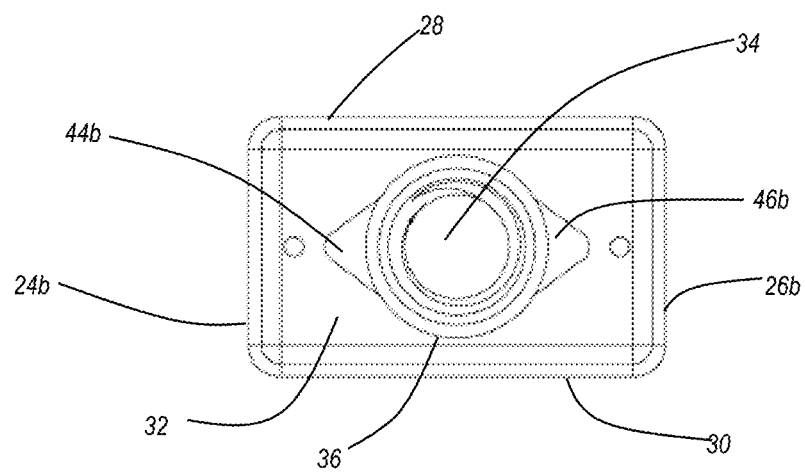
FIGS. 6A to 6C illustrate diagrammatic front, plan and side views of dental implants according to another embodiment of the invention.
Figure 6B:
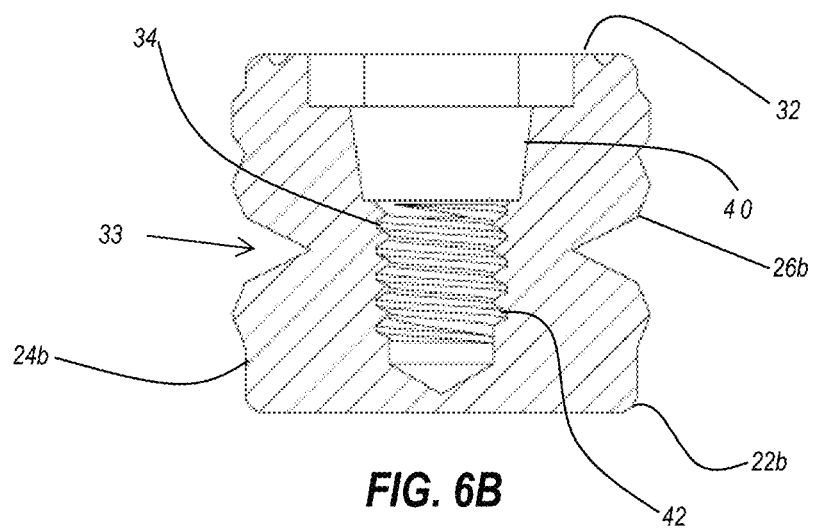
Figure 6C:
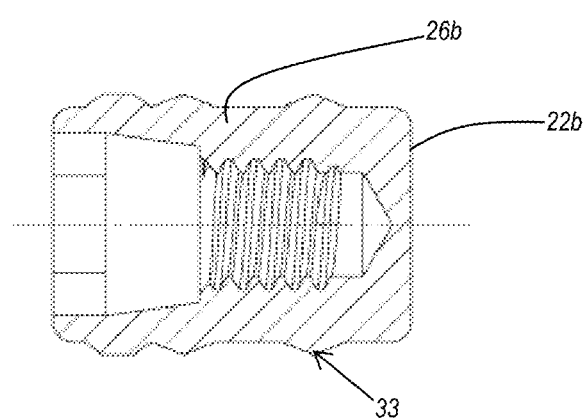
Figure 7A:
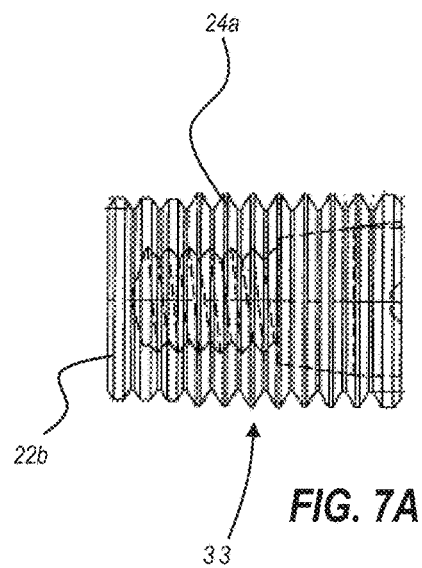
FIGS. 7A to 7C illustrate diagrammatic front, plan and side views of dental implants according to another embodiment of the invention.
Figure 7B:
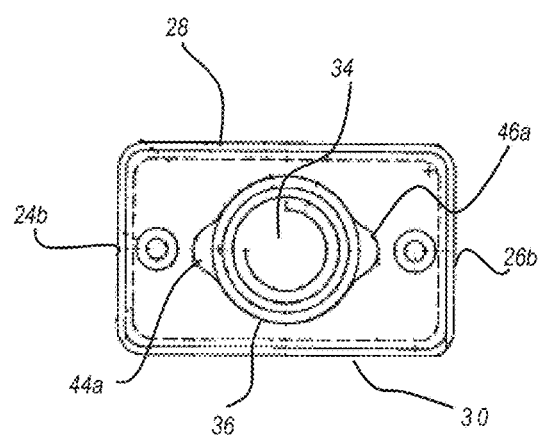
Figure 7C:
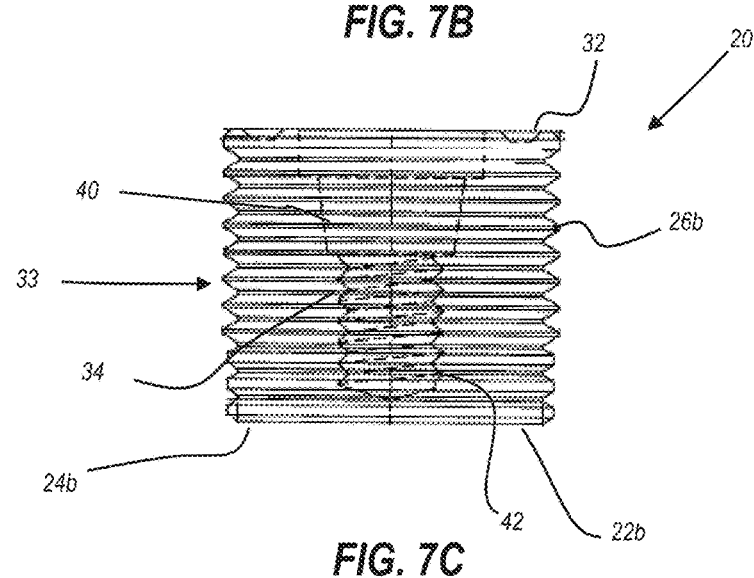
Figure 8A:
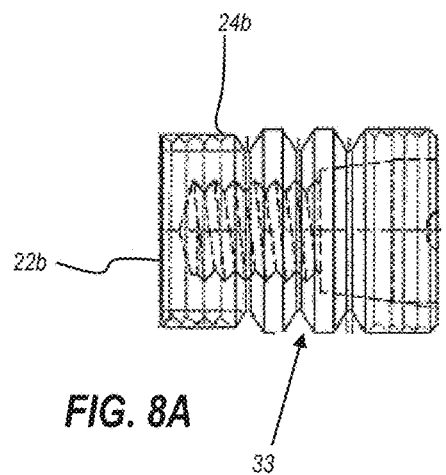
FIGS. 8A to 8C illustrate diagrammatic front, plan and side views of dental implants according to another embodiment of the invention.
Figure 8B:
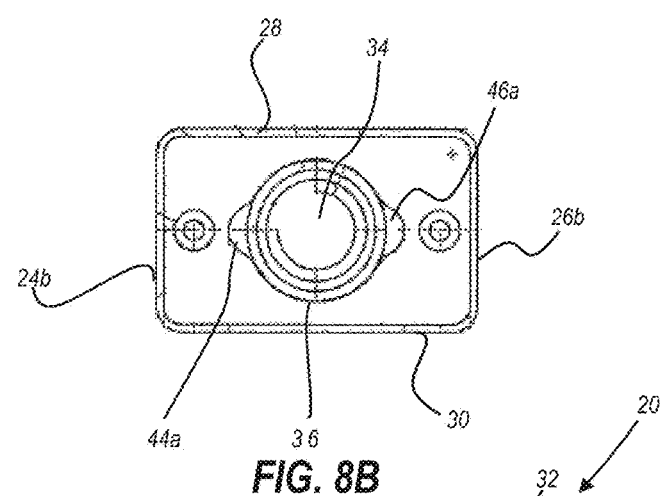
Figure 8C:
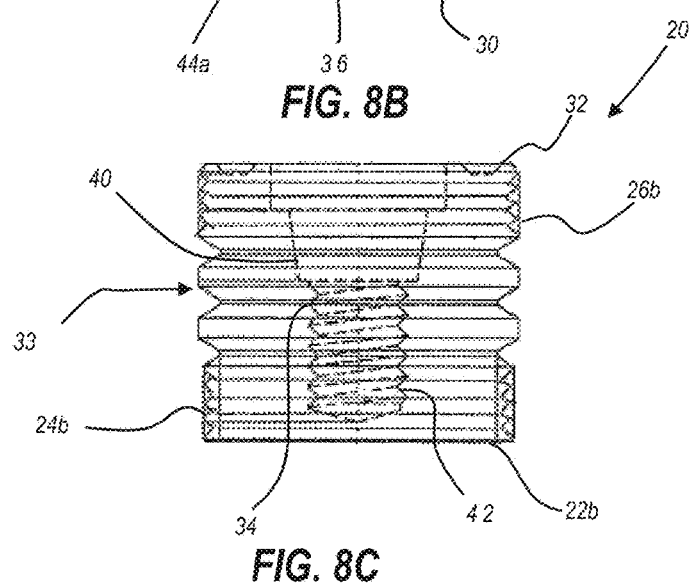
Figure 9A:
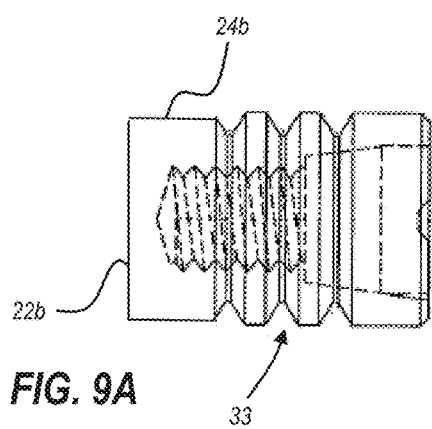
FIGS. 9A to 9C illustrate diagrammatic front, plan and side views of dental implants according to another embodiment of the invention.
Figure 9B:
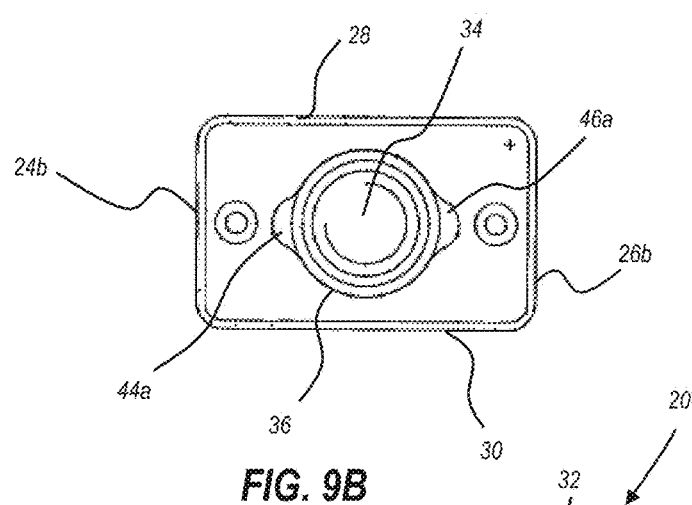
Figure 9C:
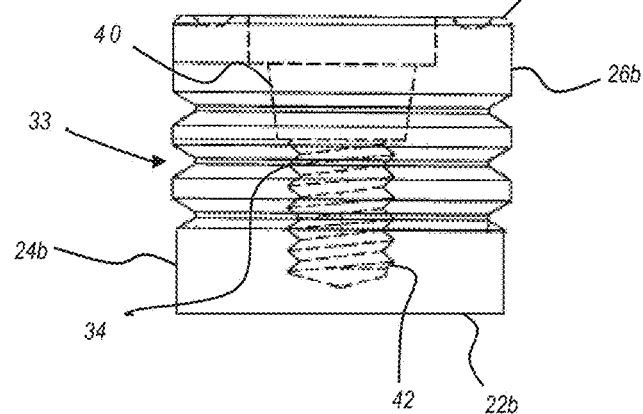

The upper surface 32 of the implant 20 is provided with a cavity in the form of an internal recess 34 and an opening 36. The internal recess 34 can be seen in shadow outline in FIGS. 5A-5C. The internal recess 34 and the opening 36 are configured for receiving a prosthetic abutment in the form of a prosthetic tooth or the like. The opening 36 is dimensioned such that it lies wholly within the upper surface 32. In some instances, the opening 36 of the recess 34 is circular. The upper end 38 of the recess 34 is formed as a truncated cone 40, which is tapered towards the threaded lower end 42 of the recess 34. The depth and angulation of the taper is dependent on the height of the implant 20. The depth of the taper will typically be up to 1.4 mm at an angular taper of up to 11°. In some arrangements, the recess 34 and the opening 36 are centrally located with respect to the upper surface 32 of the implant 20 as seen in FIGS. 5A-5C, or symmetrically located as seen in FIGS. 6A-6C. In other arrangement, the recess 34 and its corresponding opening 36 may be located anywhere along the occlusal plane.

It is to be appreciated that the opening 36 of the implant 20 is configured to receive a prosthetic abutment having an overall width or diameter smaller than the buccolingual width W of the implant 20. This configuration creates an annular set-back zone, which advantageously impedes the flow of a biofilm, between a micro-gap created upon coupling the prosthetic abutment and the implant surface 32, from reaching areas of osseointegration. More specifically, this configuration alleviates bacterial build-up around the prosthetic abutment and the implant 20, and assists in reducing further recession of the bone and the risk of subsequent implant failure. It is particularly desirable that further bone loss from bacterial infection is reduced or avoided for severely resorbed posterior alveolar ridges.

The upper surface 32 of the implant 20 is further provided with one or more shallower surface recesses that are confluent with the opening 36. In one configuration, a pair of recesses 44a, 46a are sized and shaped to receive corresponding projections provided on a prosthetic abutment which will be described in further detail below. In FIGS. 5A-5C the recesses 44a, 46a are illustrated as generally semi-circular. In another preferred embodiment recesses 44b, 46b are triangular. In other instances, a pair of recesses 44, 46 may be provided with different shapes, for example one recess may be triangular, while the other recess may be semi-circular. All these geometric variants serve as anti-rotational elements.

The anti-rotational geometry of the implant 20 is further enhanced when compared to conventional cylindrical implants. Anti-rotational features such as tri-lobes, hexagons, or octagons, provided in cylindrical implants must fit within the cylindrical diameter and are therefore their size is radially restricted due to the resultant reduction in the wall of the implant at critical minimal points. Any increase in the anti-rotational geometric diameter requires an increase in the radial diameter of the implant itself so as to avoid radial wall thinning.

In contrast, the use of the implant 20 having the form of a rectangular prism and a rectangular upper surface 32 does not impose any radial limitations on the anti-rotational geometry. Recesses 44a, 46a are advantageously provided along the longitudinal axis of the upper surface 32 of the implant 20 such that there is a residual thickness T in the ends 24a, 26a of the implant 20 (see FIGS. 5A-5C). The residual thickness T is greater than a cylindrical implant would allow, and this is further enhanced by the mesial-distal length of the implant without the need to increase the width of the implant, which as stated above is of particular concern in when placing an implant in the resorbed posterior alveolar ridge. The size of the anti-rotational recesses 44a, 46a can be increased without affecting the structural integrity of the walls of the implant 20.

The anti-rotational recesses 44a, 46a may also be increased asymmetrically, i.e. longer on one side of the opening 36 than the other side, if desired. This is not possible with a cylindrical implant as its anti-rotational geometry is also radial.

Figure 11B:
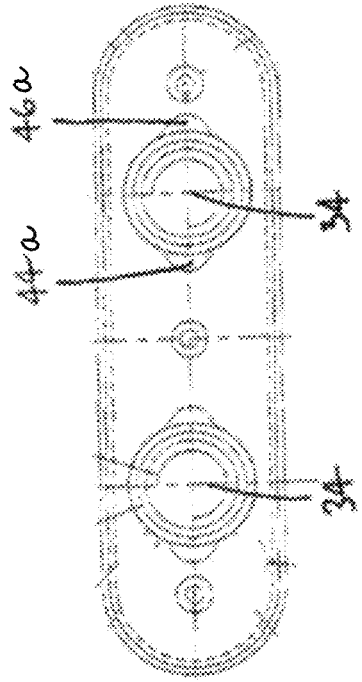
FIGS. 11A to 11O show diagrammatic front, plan and side views of a dental implant according to an embodiment of the invention.
Figure 11A:
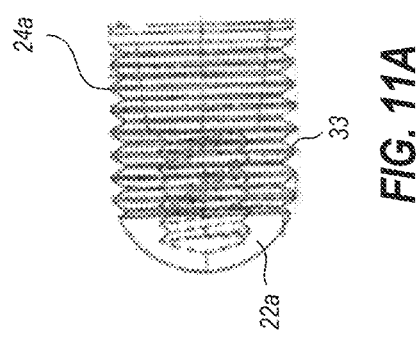
Figure 11C:
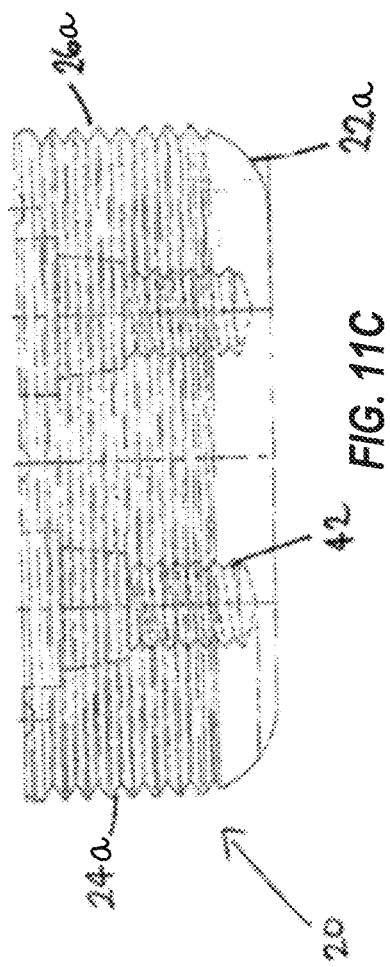

FIGS. 11A-11C illustrates an alternate embodiment of the dental implant 20. The embodiment of FIGS. 11A-11C differs in that it is a double implant, having a pair of internal recesses 34 thereby allowing two prosthetic abutments to be secured to the implant 20.

Figure 12A:
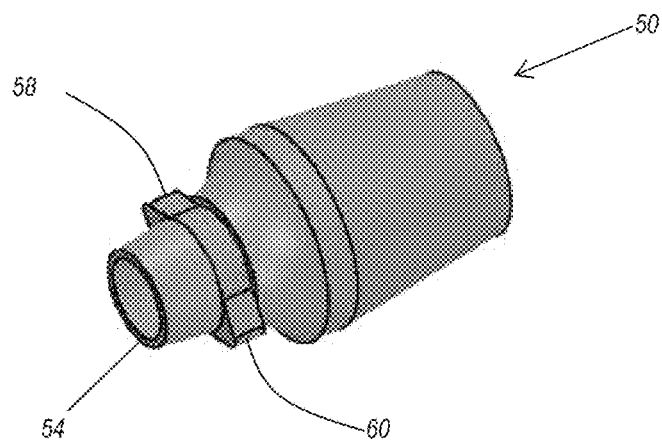
FIG. 12A is a perspective view of a prosthetic abutment for use with the dental implant of an embodiment of the invention.
Figure 12B:
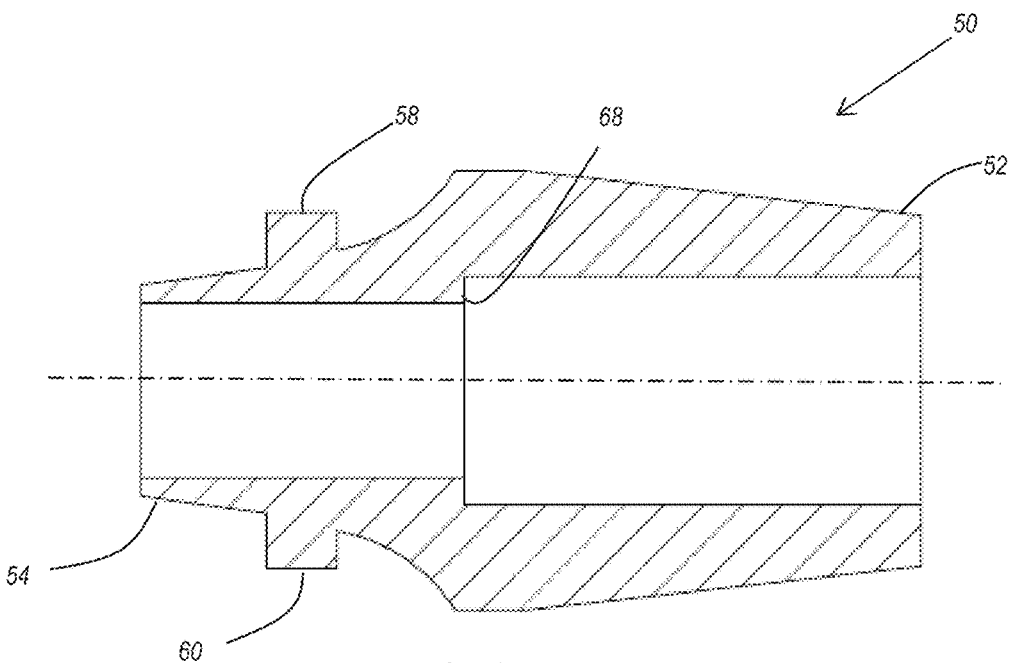
FIG. 12B is a cross-sectional view of the prosthetic abutment of FIG. 7A.

A prosthetic abutment 50 suitable for use with the dental implant 20 is shown in FIGS. 12A-12B. Abutment 50 has upper end 52 and lower end 54. Lower end 54 is a tapered cylindrical wall 56 that is dimensioned to be received in the truncated cone 40 of the implant 20 in an inference fit. The tapered cylindrical wall when received in the truncated cone 40 of the implant 20 has been shown mathematically with finite element analysis to far exceed the capacity of non-tapered internal connections for transferring shear loads of the prosthetic abutment 50 to the implant 20 and its surround bone structure. The exterior surface of the lower end 54 of the abutment may be provided with one or more anti-rotational projections. In one configuration, the abutment 50 is provided with a pair of projections 58, 60. These are illustrated as triangular prisms but other suitable shapes may be employed provided they correspond to the shapes of the recesses of implant 20.

In one configuration, anti-rotational projections 58, 60 engage in recesses 44, 46 of implant 20 when the abutment 50 is received in the truncated cone 40. Projections 58, 60 serve to prevent the abutment from rotating when the abutment 50 is secured to the implant 20.

Figure 10:
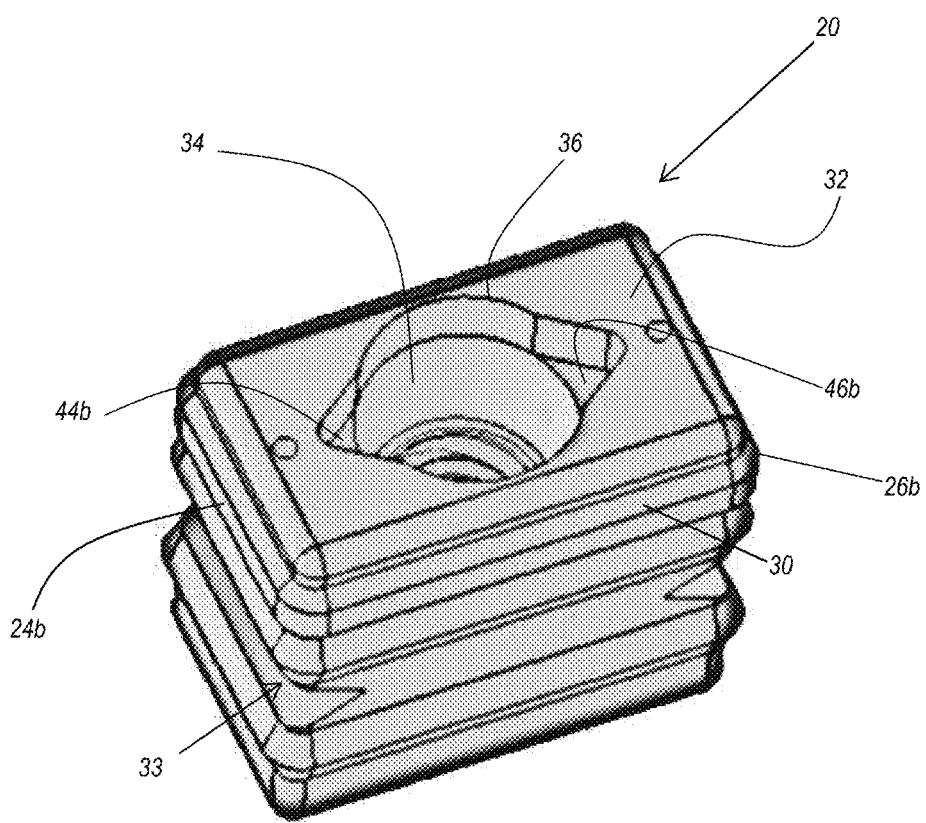
FIG. 10 is a perspective view of the implant of FIGS. 6A-6C.
Figure 13:
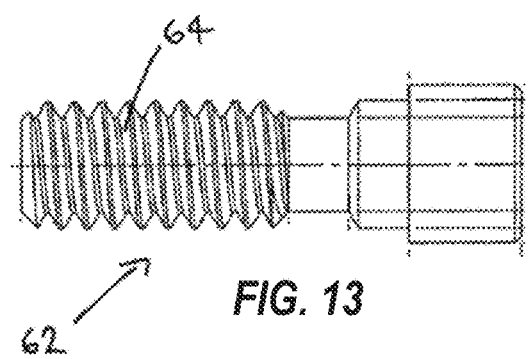
FIG. 13 is a side view of an abutment screw according to an embodiment of the invention.
Figure 14:
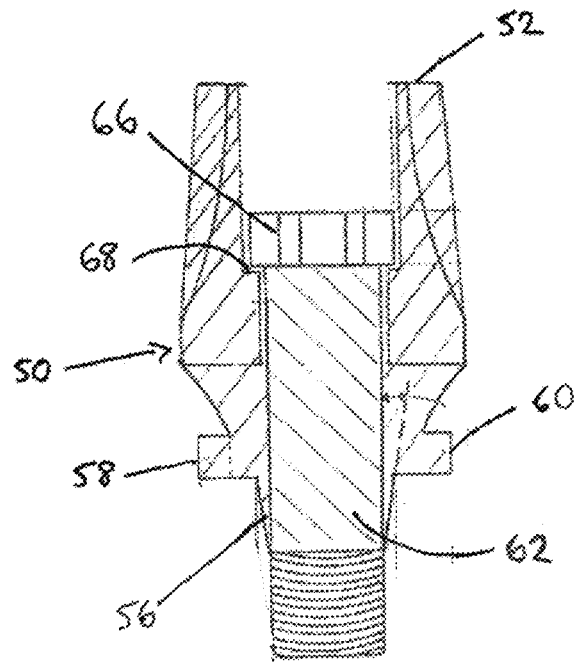
FIG. 14 is a side cross-sectional view of an abutment screw received within a prosthetic abutment according to an embodiment of the invention.
Figure 15:
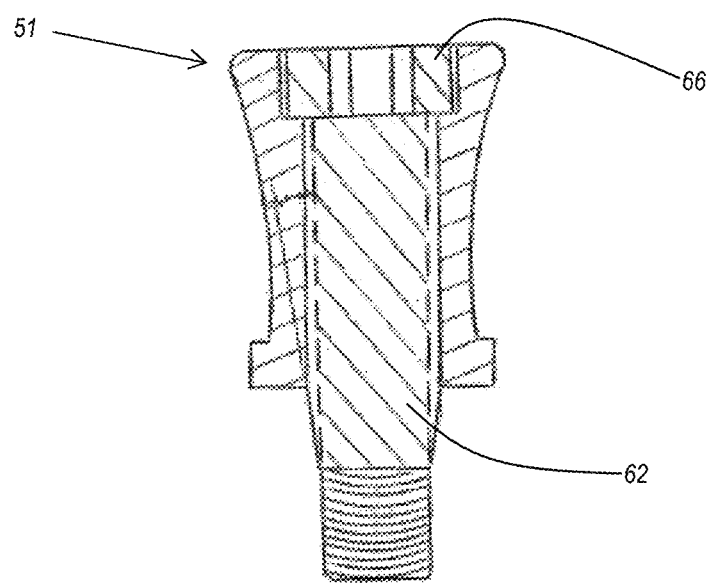
FIG. 15 is a side cross-sectional view of an abutment screw received within a healing abutment according to an embodiment of the invention.
Figure 16:
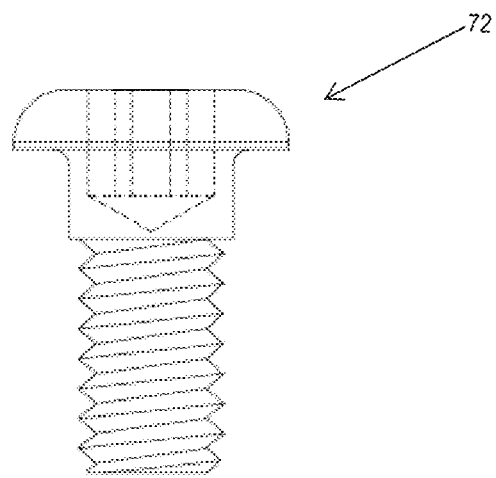
FIG. 16 is a front view of a cover screw for use with the dental implant of an embodiment of the invention.
Figure 17:
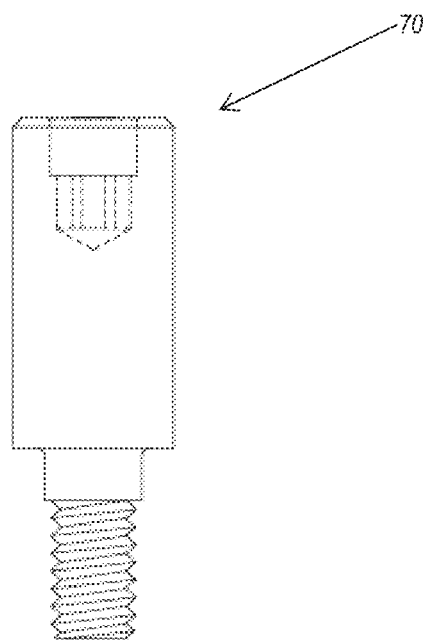
FIG. 17 is a front view of an installation tool for use with the dental implant of an embodiment of the invention.
Figure 18:
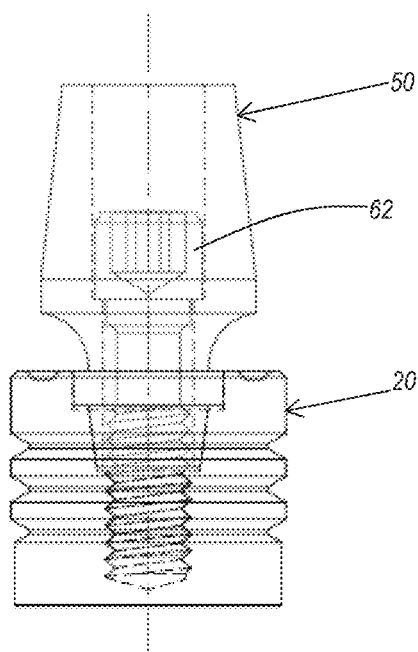
FIG. 18 is a front view of an assembly of an implant with an abutment and abutment screw according to an embodiment of the invention.
Figure 19:
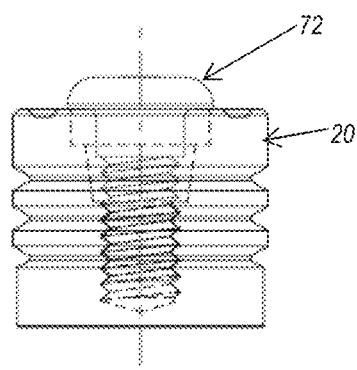
FIG. 19 is a front view of an assembly of an implant with a cover screw according to an embodiment of the invention.
Figure 20:
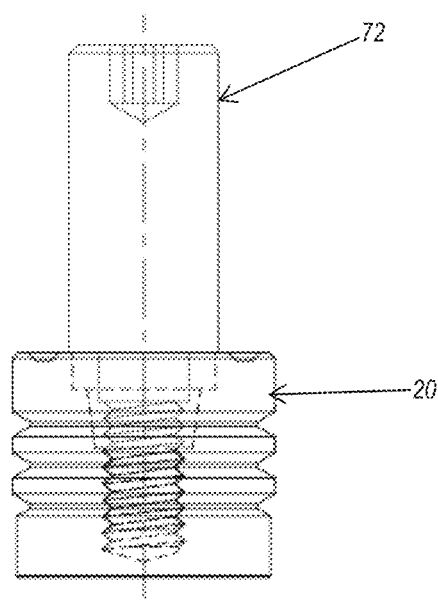
FIG. 20 is a front view of an assembly of an implant with an installation tool according to an embodiment of the invention.

With reference to FIGS. 13-15, abutment 50 is secured to implant 20 using an abutment fastener in the form of a screw 62. The interaction between the abutment screw 62 and abutment 50 is illustrated in FIG. 14. In one configuration, a healing abutment 51 is secured to the implant 20 using the abutment screw 62 as shown in FIG. 10. Screw 62 passes centrally through the abutment 50 and the lower end 64 of the screw 62 threadingly engages the lower end 42 of recess 34 as shown in FIGS. 5A-5C. The abutment 50 is screwed into the recess 34 until the anti-rotational projections 58, 60 engage with corresponding recesses 44a, 46a.

In addition to the screw fastening engagement, the tapered cylindrical wall 56 forms an interference fit with the truncated cone 40 of the implant. The head 66 of the abutment screw 62 also acts on internal shoulder 68 of the abutment 50 effectively pushing the abutment 50 into recess 34 thereby enhancing stability. A tapered integrated screw connection is thus formed between the tapered lower end 54 of the abutment 50 and the truncated cone 40 of the implant 20 when the abutment 50 is screwed to the implant 50. Advantageously, this tapered integrated screw design reduces the ratio of loosening to tightening torque and therefore improves resistance to the effect of screw loosening.

The abutment 50 and abutment screw 62 are preferably formed of Grade IV Titanium. In some embodiments, the abutment 50 is formed of Grade V Titanium and abutment screw 62 is formed of commercially gold screw or Grade V Titanium (with 2 mm diameter—type M2). In another embodiment, the implant 20 is preferably formed of type IV Titanium.

In one arrangement, a dental implant system or kit is provided, including at least one horizontally-oriented dental implant 20 and a prosthetic abutment 50 of the present disclosure, with the implant 20 and the abutment 50 being configured to detachably join to one another with a tapered integrated screw arrangement of the present disclosure, and corresponding anti-rotational elements to prevent rotation of the abutment 50 about the implant 20.

A dental implant system or kit may further include a set of pre-configured implants 20 and abutments 50 of varying shapes and sizes prepared for the dental clinician to choose from. For example, the implant 20 may have various configurations including single or multiple abutment variations, with different sizes and surface geometry (for example, grooves) configurations. A kit may include implants of different mesial-distal lengths of 6 mm, 8 mm and 10 mm, as well as appropriate customised surgical peizotome ultrasonic tools to suit the implant size. The abutment 50 may be chosen from a selection of suitable configurations, including healing abutment and abutments to replace bicuspids, molar, canines or incisors. The dental clinician may choose the implant system or kit parts that are appropriate for the particular application.

In some instances, the dental professional may arrange for the implant 20 and/or the abutment 50 to be custom made. For example, the side wall curvature of the implant 20 may be curved to substantially match the curvature of a patient's posterior alveolar ridge, thus tailoring the implant to a patient's morphology.

A method of restoring the resorbed posterior alveolar ridge of a jaw bone using an implant 20 of the present disclosure is also provided. The method utilises piezo-ultrasonics to create the surgical defect to receive the implant. With reference to FIGS. 16 to 19, in general steps, an ultrasonic osteotome is used to mark the alveolar ridge after the mucosa and its periosteum have been reflected, then the various spades such as ultrasonic osteotomes facilitates harvesting of the bone tissues. The osteotomy completed is generally rectangular in outline and its depth corresponds to the height of the implant. The seating of the implant is a press fit action, crucially facilitated by the mesial and distal dimples on the crestal surface of the implant. The maneuvering and handling of the implant until final seating can also be aided by the engagement of an installation tool 70 in the form of a handle like cylinder which engages the internal thread 42 of the implant 20. The length of the installation tool is variable and could be up to 3 mm in length. Final seating is a press fit action with the use of a mallet and centre-punches which engage the dimples, and the rim of the main recess. After the implant has been set, the recess and opening of the implant may be closed by fixing a cover screw 72 to the installed implant using the tapered connection screw arrangement of the present disclosure. Bone harvested from the action of the ultrasonic osteotomy preparation can then be used to back fill surgical defects and augment the alveolus generally without the need for further donor sites. The mucoperioteal tissues are then replaced, and healing occurs superficially. A process of osseointegration occurs thereafter (up to 12 weeks are required for osseointegration to occur) wherein the bone structure heals in contact with the implant. After this time frame (now post integration) a surface incision is made to expose the underlying cover screw. The cover screw is removed, and a healing abutment is engaged. This latter structure is designed to facilitate surface soft tissue healing only, such that in later steps—impression taking and final prosthetic seating—no further incisions will be needed. After integration has been achieved, a dental clinician can then remove the healing prosthetic and secure a new prosthetic tooth or other dental prosthesis to the implant using the same tapered connection screw arrangement.

The method advantageously reuses the harvested bone tissues and cells for installing the implant 20, which avoids the need for bone grating (autograft) such as taking bone tissues from a different site along the jaw. The ability to reuse the harvest bone tissues (for example, trabecular bone—soft and spongy to fill in the small gaps easily) to refill the gaps around the implant reduces the surgical steps and time involved in the procedure and the number of invasive cuts required for the jaw bone, which is beneficial to both the dental clinician and the patient.

The applicant notes that with respect to the manufacturing of the implant 20, lathe turning (for example, CNC machining) provides lower tolerances than modern multi-axis milling machining—this was examined through micro computerised tomography of repeated manufacturing runs. Further, with respect to the internal implant geometry, the tolerance of manufacture is an important element in the construction of the implant 20. The truncated cone 40 should have the lowest tolerance in manufacture, the tolerance being less than 5 micrometres. This low tolerance yields efficient coupling and interfacial force transfer. In order to achieve this however, the anti-rotational geometry must be manufactured with a higher tolerance (an order of magnitude higher), such that the interference between the competing geometries is reduced or eliminated. A preference is given to the coupling of the truncated cone 40 and the tapered cylindrical wall 56 of the abutment 50, as this has been proven mathematically to be the predominant mechanism of interfacial shear and normal force transfer within the implant 20. This efficient force transfer between the truncated cone 40 and the abutment 50 goes some way towards protecting against the loosening of the abutment screw 62. On the other hand, the manufacture tolerance is not a major factor with respect to the external geometry of the implant 20, as irregularities will allow for an overall increase of external macro surface area.

Experimentation Results:

Fatigue analysis of a preferred embodiment of the present invention was conducted using the modified ISO 14801 protocol. The protocol was applied to the embedded implant abutment-crown complex and yielded a result of 2,500 N at approximately $5 \times 10^5$ cycles (simulated mastication) before catastrophic component failure. This failure occurred at the level of the first thread of the abutment screw and correspondingly horizontally through the truncated cone of the prosthetic abutment. Further, the maximum vertical masticatory force determined from the experiment is in the range of 700-800 N. This yields an approximate three fold greater tolerance of the assembly componentry than what is required in the masticatory force environment.

Although the steps described above is provided in a specific order, it can be performed in any variation of this order and additional steps may be executed between the steps described above.

It will appreciated that the dental implant of the invention resolves many of the issues faced by surgeons and patients alike, when faced with prosthodontic reconstruction in a resorbed posterior alveolar ridge. In combination with the prosthetic abutment described, the dental implant provides the maximum osseointegration available while securely receiving the prosthetic abutment in a robust anti-rotational interference fit.

It will be understood that the invention disclosed and defined in this specification extends to all alternative combinations of two or more of the individual features mentioned or evident from the text or drawings. All of these different combinations constitute various alternative aspects of the invention.

In the description and drawings of this embodiment, same reference numerals are used as have been used in respect of the first embodiment, to denote and refer to corresponding features.

While various embodiments of the present invention have been described above, it should be understood that they have been presented by way of example only, and not by way of limitation. It will be apparent to a person skilled in the relevant art that various changes in form and detail can be made therein without departing from the spirit and scope of the invention. Thus, the present invention should not be limited by any of the above described exemplary embodiments.

The invention claimed is:

1. A dental implant adapted for implanting within a jaw bone, the implant comprising a horizontally-oriented body having a length extending in the mesial-distal direction of the jaw bone, the horizontally-oriented body having a cavity dimensioned for receiving a prosthetic abutment, wherein the cavity comprises:
   (1) an opening that is located wholly within a buccolingual width of the horizontally-oriented body; and
   (2) sides that are fully enclosed within the width of the horizontally-oriented body;
   (3) a truncated conical portion at a upper end of the cavity;
   wherein the horizontally-oriented body is configured to substantially reside within a generally rectangular prism shape having a minimum buccolingual width of 4 mm, a minimum apical-occlusal height of at least 5 mm, and a minimum mesial-distal length of 6 mm, wherein the horizontally-oriented body comprises a rounded base, and wherein one or more surface recesses are provided in an upper surface of the dental implant for receiving anti-rotational projections, with the surface recesses being confluent with, and completely embedded within, the upper end of the cavity.

2. A dental implant of claim 1, wherein the horizontally-oriented body has substantially the same buccolingual width along its mesial-distal length.

3. A dental implant of claim 1, wherein the horizontally-oriented body has two end walls, two side walls, and a base that, together with the upper surface, form external surfaces of the horizontally-oriented body.

4. A dental implant of claim 3, wherein one or more external surfaces of the horizontally-oriented body are provided with a plurality of surface geometry for enhancing the surface area of the horizontally-oriented body.

5. A dental implant of claim 4, wherein the plurality of surface geometry includes any one or more of the following: grooved, ridged, gouged, wavy or cratered.

6. A dental implant of claim 5, wherein a plurality of grooves are provided on the two end faces and the two side faces.

7. A dental implant of claim 5, wherein the plurality of grooves are provided on the base of the horizontally-oriented body.

8. A dental implant of claim 5, wherein the shape of the grooves includes any one or more of the following: v-shaped, rounded, circular, semi-circular, triangular, trapezoidal, or irregular in shape.

9. A dental implant of claim 5, wherein the grooves are of equal width.

10. A dental implant of claim 5, wherein the grooves are smaller in width in a crestal portion of the horizontally-oriented body.

11. A dental implant of claim 4, wherein the surface of the horizontally-oriented body comprises a plurality of grooves extending along a horizontal axis of the horizontally-oriented body.

12. A dental implant of claim 3, wherein the base of the horizontally-oriented body is flat and the horizontally-oriented body has straight side walls.

13. A dental implant of claim 3, wherein the horizontally-oriented body is formed with curved end walls.

14. A dental implant of claim 3, wherein the horizontally-oriented body is formed with straight end walls.

15. A dental implant of claim 1, wherein the horizontally-oriented body is substantially trapezoidal in shape with a wider crestal portion and a smaller apical portion.

16. A dental implant of claim 1, wherein the horizontally-oriented body is formed of titanium.

17. A dental implant of claim 1, wherein a cylindrical internal thread is provided at the lower end of the cavity.

18. A dental implant system for implanting within a jaw bone, the system comprising:
a dental implant as in claim 1;
wherein the cavity of the dental implant is threaded;
at least one prosthetic abutment comprising an external tapered connection and an internal recess, wherein the at least one prosthetic abutment is dimensioned and adapted to be received by the cavity of dental implant by way of interference fit; and
an abutment fastener for securing the abutment to the horizontally-oriented body, wherein the fastener is received within the internal recess of the abutment and secured to the threaded cavity of the dental implant.

19. A dental implant system of claim 18, wherein the prosthetic abutment is provided on its outer surface with a pair of opposed anti-rotational projections.

20. A dental implant system of claim 19, wherein the shape of the projections includes any one or more of the following non-limiting examples: triangular or semi-circular prisms.

21. A dental implant system of claim 19, wherein the horizontally-oriented body further comprises at least one surface recess having dimensions corresponding to the opposed anti-rotational projections, such that, in use, the prosthetic abutment is received in a truncated conical portion provided at the upper end of the cavity and secured in place such that the opposed projections align with and engage the corresponding surface recesses.

22. A method for restoring a resorbed posterior alveolar ridge of a jaw bone using a dental implant system, the method comprising the steps of:
providing a dental implant as in claim 1;
providing a prosthetic abutment having an internal recess to the dental implant by way of securing an abutment fastener through the internal recess of the prosthetic abutment to the cavity of the horizontally-oriented body.

23. A method of claim 22, further comprising the steps of:
excavating an implant site at the resorbed posterior alveolar ridge of a jaw bone;
seating the dental implant at the implant site;
filling the implant site with bone tissue materials harvested during the excavation of the implant site; and
closing the implant site with sutures.

24. A dental implant of claim 1, wherein the surface recesses are mesial-distally oriented.

25. A dental implant of claim 1, wherein the shape of the surface recesses is either triangular or semi-circular.

* * * * *